United States Patent
Cor et al.

(10) Patent No.: US 10,154,671 B2
(45) Date of Patent: Dec. 18, 2018

(54) BACTERIAL COMPOSITION FOR IMPROVING PLANT GROWTH

(71) Applicant: LALLEMAND PLANT CARE SAS, Castelmaurou (FR)

(72) Inventors: Olivier Cor, Toulouse (FR); Bruno Sanchez, Castelmaurou (FR)

(73) Assignee: DANSTAR FERMENT AG, Zug (CH)

( * ) Notice: Subject to any disclaimer, the term of this patent is extended or adjusted under 35 U.S.C. 154(b) by 29 days.

(21) Appl. No.: 14/439,676

(22) PCT Filed: Oct. 30, 2013

(86) PCT No.: PCT/IB2013/059795
§ 371 (c)(1),
(2) Date: Jul. 6, 2015

(87) PCT Pub. No.: WO2014/068501
PCT Pub. Date: May 8, 2014

(65) Prior Publication Data
US 2015/0342198 A1    Dec. 3, 2015

(30) Foreign Application Priority Data
Oct. 30, 2012  (FR) ...................... 12 60339

(51) Int. Cl.
*A01N 63/00*    (2006.01)
*A01N 63/04*    (2006.01)

(52) U.S. Cl.
CPC ............ *A01N 63/04* (2013.01); *A01N 63/00* (2013.01)

(58) Field of Classification Search
None
See application file for complete search history.

(56) References Cited

U.S. PATENT DOCUMENTS

| 2009/0169530 A1 | 7/2009 | Tsuda et al. | |
| 2011/0269119 A1* | 11/2011 | Hutchison | C12Q 1/6806 435/6.1 |
| 2013/0269719 A1* | 10/2013 | Marshall | A24B 15/245 131/290 |

FOREIGN PATENT DOCUMENTS

| CN | 101440007 | * | 5/2009 |
| WO | 2006/089416 A2 | | 8/2006 |

OTHER PUBLICATIONS

Champagne et al.(Viability of Lactobacillus Rhamnosus R0011 in an Apple-Based Fruity Juice under Simulated Storage Conditions at the Consumer Level(Journal of Food Science, vol. 73, Nr. 5, 2008.*
Xymogen: "Lacidofil Product Label ", https://www.xymogen.com/products/product-d etail.aspx?pid=103, Feb. 29, 2012 (Feb. 29, 2012), p. 1, XP055062081, Orlando Florida Retrieved from the Internet: URL:https://www.xymogen.com/assets/imageDi splay.ashx?formulaID=103&attachmentTypeID= 5 [retrieved on May 7, 2013] the whole document.
Champagne C P et al.: "Viability of Lactobacillus rhamnosus R0011 in an apple-based fruit juice under simulated storage conditions at the consumer level", Journal of Food Science. Wiley-Blackwell Publishing. Inc. US, vol. 73. No. 5. Jun. 1, 2008 (Jun. 1, 2008), pp. M221-M2226. XP009140699, ISSN: 0022-1147. 001: 10.IIII/J.1750-3841.2008.00775.X [retrieved on Jun. 9, 2008] the whole document.
International Search Report, dated Feb. 4, 2014, from corresponding PCT application.

* cited by examiner

*Primary Examiner* — Alton N Pryor
(74) *Attorney, Agent, or Firm* — Young & Thompson

(57) ABSTRACT

A composition and method for improving plant growth, wherein the composition includes at least one live strain of bacteria of the *Lactobacillus rhamnosus* species.

19 Claims, 1 Drawing Sheet

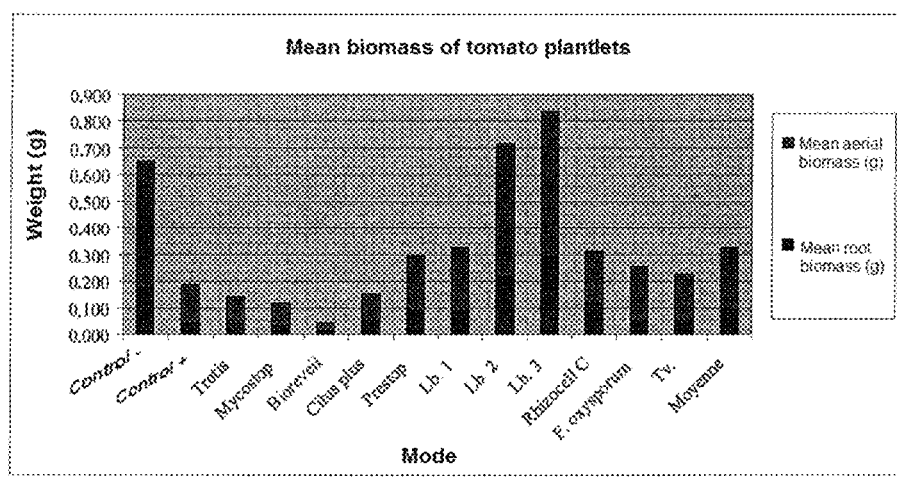

BACTERIAL COMPOSITION FOR IMPROVING PLANT GROWTH

FIELD OF THE INVENTION

The invention is directed to a composition for improving plant growth.

BACKGROUND OF THE INVENTION

In the agriculture field, increasing production efficiencies remains a key issue both economically and socially. For this, numerous chemical or biological compositions have been suggested and led to variable efficiency results. They aim at (i) directly controlling crop pests, (ii) protecting plants from abiotic stresses, (iii) stimulating natural defences and (iv) improving plant nutrition and growth.

SUMMARY OF THE INVENTION

Within this context, the inventors have noticed that, surprisingly, a particular *Lactobacillus* species exerted remarkably higher effects, in terms of plant growth and protection, than those obtained with other species from the *Lactobacillus* genus or referenced antifungal compounds. This surprising effect on plant growth can be accompanied with a more predictable protective effect towards some fungi.

Therefore, the purpose of the invention is to provide a new highly efficient composition for improving plant growth.

It also aims at taking advantage of the properties of such a composition in a method aiming at improving plant growth.

The composition of the invention for improving plant growth is characterised in that it comprises at least one bacterium live strain of the *Lactobacillus rhamnosus* species.

The *Lactobacillus rhamnosus* strain deposited at the CNCM under no. I-1720 on Jul. 1, 1996, is particularly advantageous to ensure this growth.

BRIEF DESCRIPTION OF THE DRAWING

FIG. 1 illustrates the effect of different microbial treatments on mean biomass (root biomass and aerial biomass) of tomato plantlets.

DETAILED DESCRIPTION OF THE INVENTION

In one embodiment, the composition of the invention is characterised in that it comprises said bacterium (bacteria) in combination with other live, inactivated or extract microorganisms (yeasts, bacteria and/or fungi).

In another embodiment of the invention, the composition will further include advantageously live or inactivated micro-organisms, micro-organisms extracts, fertilisers, herbicides, insecticides, fungicides, mineral solutions and/or growing media.

The invention is also directed to formulations of the composition for soil treatments, root part treatment, foliar treatment and/or seed treatment.

Suitable formulations comprise powders, in particular wettable powders, granules, micro-granules, seed treatments, liquid formulations, in particular suspensions of the compositions of the invention in water and bacteria encapsulations.

The suitable formulation contains from $10^6$ to $10^{12}$ CFU/g, in particular from $10^8$ to $10^{10}$ CFU/g of *Lactobacillus rhamnosus*.

These formulations are packaged in packages preserving them from any degradation, preferably stored at temperatures not exceeding 20° C. Such formulations are stable and can be preserved during at least 10 months.

The invention further relates to a method for improving plant growth, characterised by applying onto the seed, the soil, the root or foliar part of the plant, for example by spraying a powder or a liquid formulation, in particular a water suspension, a composition as defined above.

Repeated applications, for example every 3 to 6 weeks, according to doses ranging from 13 to 30 mg/plant or 150 to 250 g/Ha, preferably on the seed or at the emergence, at the early stages of flowering, seem favourable to the plant development and increase the growth thereof.

The application of the composition and method, defined above, to grain crops (wheat, barley, oats, rye), row crops (sugar beet, potato, corn), legume crops (alfalfa, clover, sainfoin), gramineae (rye-grass, fescue, orchard grass, festulolium), oil and protein seed crops (soy, rapeseed, peas, field bean, white lupine), market gardening and vegetable crops, fruit farming, viticulture and ornamental crops (flower productions, young plant nursery) have a particular interest.

Further characteristics and advantages of the invention are given by way of illustrating purposes in the examples that follow and on the single figure which reports test results on tomato plants in growth chambers.

EXAMPLE 1

Preparation of a Composition Based on *Lactobacillus rhamnosus*

This composition is made from:
Growth stimulating micro-granules (10 kg/ha) comprising:
- 2% of *Lactobacillus rhamnosus*, that is 200 g/Ha
- 1.0% of yeast derivatives, that is 100 g/Ha
- 1.5% of "symbiotic fungi" *Glomus intraradices*, that is 150 g/Ha

EXAMPLE 2

Formulation for Seed Application 2.6 g/kg *Lactobacillus rhamnosus* on seeds of a PMG 48 straw grain

EXAMPLE 3

Application to Tomato Crops

The tests of which results are reported hereinafter have been conducted according to the following protocol:

The test made includes 13 modes (10 formulations of micro-organisms and 3 controls (a positive control with *Fusarium oxysporum* f. sp. *lycopersici* race 0, a negative control without pathogen, a chemical reference control made with a contact fungicide, TROTIS® used at 5%)). On these 13 modes, 15 repetitions have been made, that is a total of 195 tomato plantlets.

The *Lactobacillus rhamnosus* dose is 13 mg per plant at $1.44 \cdot 10^9$ CFU/g.

The substrate used is a mixture of 3 volumes of a local soil, sampled from a field of an organic farm, and 2 volumes of washed siliceous sand with a particle size between 0.3 and 1 mm. The analysis of this soil is provided in the following table:

TABLE

| PARAMETER | METHOD | UNIT | RESULT |
|---|---|---|---|
| pH $H_2O$ | Potentiometry | — | 7.5 |
| pH KCl | Potentiometry | — | 7.1 |
| Oxidizable organic matter | Potassium dichromate RedOx titration | % ppm | 3.20 |
| Macro-elements | | | |
| Total phosphorus | $HClO_4$ UV/VIS | mg/kg | 36 |
| Total nitrogen | Kjeldahl | % p/p | 0.29 |
| Olsen phosphorus | Sodium bicarbonate UV/VIS | mg/kg | 78 |
| Potassium | $CINH_4$ | mg/kg | 1329 |
| Calcium | $CINH_4$ | mg/kg | 1770 |
| Magnesium | $CINH_4$ | mg/kg | 200 |
| Sodium | $CINH_4$ | mg/kg | 240 |
| CEC | Sodium acetate | meq/100 g | 20 |
| Micro-elements | | | |
| Assimilable iron | EDTA | mg/kg | 51 |
| Assimilable manganese | EDTA | mg/kg | 16 |
| Assimilable copper | EDTA | mg/kg | 4 |
| Assimilable zinc | EDTA | mg/kg | 10 |
| Characterization of the mixture | | | |
| Sands | Bouyoucos | % pp | 44 |
| Loams | Bouyoucos | % pp | 25 |
| Clays | Bouyoucos | % pp | 27 |

The tomato seeds have been washed beforehand in a 10% bleach water bath, washed with water, rehydrated for 24 h before being sown. The plants have been watered with a Hewitt nutrient solution.

The results are given in the single figure. The compounds used in the test are the following ones:

Negative control: control without treatment, without inoculation of the pathogen Positive control: control without treatment, with inoculation of the pathogen Trotis®: antifungal Mycostop: *Streptomyces* sp. based antifungal Bioréveil: yeast extracts Cilus plus: *Bacillus* sp.

Prestop: antifungal

Lb1: *Lactobacillus acidophilus*

Lb2: *Lactobacillus plantarum*

Lb3: *Lactobacillus rhamnosus*

Rhizocell: *Bacillus* sp.

*Fusarium oxysporum*: non-pathogen fungus strain

Tv.: ascomycete

As shown by the results obtained in this test, the mean biomass of the tomato plantlets (root biomass and aerial biomass) is remarkably higher in comparison with that obtained with usual products, and even with bacteria of the same genus.

Surprisingly, the tomatoes that have received treatments with *Lactobacillus rhamnosus* even though initially infected, have a higher development than healthy controls.

The invention claimed is:

1. A composition for improving plant growth, comprising at least one bacterium live strain of the *Lactobacillus rhamnosus* species, in combination with at least one inactivated or extract fungi and/or yeast, wherein *Lactobacillus rhamnosus* is the only *Lactobacillus* species present in the composition and wherein the at least one bacterium live strain of the *Lactobacillus rhamnosus* species improves plant growth over an untreated plant with or without exposure to a pathogen.

2. The composition according to claim 1, wherein the at least one bacterium is the *Lactobacillus rhamnosus* strain deposited at the CNCM under No. I-1720 on Jul. 1, 1996.

3. The composition according to claim 1, further comprising fertilizers, herbicides, insecticides, a fungicide or fungicides, mineral solutions and/or growing media.

4. The composition according to claim 1, wherein the composition is in a form suitable for soil treatment, root part treatment, foliar treatment and/or seed treatment.

5. The composition according to claim 4, wherein the composition is in the form of a powder, wettable powder, granules, micro-granules, seed treatment, liquid formulation, water suspension or bacteria encapsulations.

6. The composition according to claim 1, comprising $10^6$ to $10^{12}$ CFU/g of *Lactobacillus rhamnosus*.

7. A method for improving plant growth over an untreated plant with or without exposure to a pathogen and capable of protecting plants against fungi, comprising applying onto the seed, the soil, the root or the foliar part of the plant by spraying the composition according to claim 6.

8. The method according to claim 7, wherein the composition is applied to grain crops, row crops, legume crops, gramineae, oil and protein seed crops, market gardening and vegetable crops, fruit farming crops, viticulture and ornamental crops, flower production crops, or young nursery plants.

9. A method for improving plant growth over an untreated plant with or without exposure to a pathogen and capable of protecting plants toward some fungi, comprising applying onto the seed, the soil, the root or the foliar part of the plant by spraying a composition comprising a bacterium live strain of the *Lactobacillus rhamnosus* species, said *Lactobacillus rhamnosus* being the only *Lactobacillus* species present in the composition, and said composition being in a form suitable for soil treatment, root part treatment, foliar treatment and/or seed treatment wherein the bacterium live strain of the *Lactobacillus rhamnosus* species improves plant growth over an untreated plant with or without exposure to a pathogen.

10. The method according to claim 9, wherein said applying comprises spraying a powder, a liquid formulation, or a water suspension of the composition.

11. The method according to claim 9, wherein the composition is applied to grain crops, row crops, legume crops, gramineae, oil and protein seed crops, market gardening and vegetable crops, fruit farming crops, viticulture and ornamental crops, flower production crops, or young nursery plants.

12. The composition according to claim 2, further comprising fertilizers, herbicides, insecticides, a fungicide or fungicides, mineral solutions and/or growing media.

13. The composition according to claim 1, comprising $10^8$ to $10^{10}$ CFU/g of *Lactobacillus rhamnosus*.

14. A composition, comprising at least one bacterium live strain of the *Lactobacillus rhamnosus* species, wherein *Lactobacillus rhamnosus* is the only *Lactobacillus* species present in the composition, wherein said composition is in a suitable formulation for soil treatment, root part treatment, foliar treatment and/or seed treatment, and the at least one bacterium live strain of the *Lactobacillus rhamnosus* species provides an improvement in plant growth over an untreated plant with or without exposure to a pathogen.

15. The composition according to claim 14, comprising the *Lactobacillus rhamnosus* strain deposited at the CNCM under no. I-1720 on Jul. 1, 1996.

16. The composition according to claim 14, wherein the composition further comprises fertilizers, herbicides, insecticides, a fungicide or fungicides, mineral solutions and/or growing media.

17. The composition according to claim 14, wherein the composition is in the form of a powder, wettable powder, granules, micro-granules, seed treatments, liquid formulations, or bacteria encapsulations.

18. The composition according to claim 14, comprising $10^6$ to $10^{12}$ CFU/g of *Lactobacillus rhamnosus*.

19. The composition according to claim 14, comprising $10^8$ to $10^{10}$ CFU/g of *Lactobacillus rhamnosus*.

* * * * *